US007803929B2

(12) United States Patent
Melkonyan et al.

(10) Patent No.: US 7,803,929 B2
(45) Date of Patent: Sep. 28, 2010

(54) KITS FOR DIAGNOSIS AND MONITORING OF PATHOGENIC INFECTION BY ANALYSIS OF CELL-FREE PATHOGENIC NUCLEIC ACIDS IN URINE

(75) Inventors: Hovsep Melkonyan, Princeton, NJ (US); Angela Cannas, Arbus (IT); Louis David Tomei, Genazzano (IT); Samuil R. Umansky, Princeton, NJ (US)

(73) Assignee: TrovaGene, Inc., San Diego, CA (US)

( * ) Notice: Subject to any disclaimer, the term of this patent is extended or adjusted under 35 U.S.C. 154(b) by 310 days.

(21) Appl. No.: 11/137,934

(22) Filed: May 25, 2005

(65) Prior Publication Data

US 2006/0183107 A1    Aug. 17, 2006

(30) Foreign Application Priority Data

Feb. 17, 2005    (IT)    .................. RM2005A0068

(51) Int. Cl.
*C07H 21/04*    (2006.01)
*A61K 9/14*    (2006.01)
*C12N 9/12*    (2006.01)

(52) U.S. Cl. .................... 536/24.33; 424/484; 435/194; 435/810

(58) Field of Classification Search ........................ None
See application file for complete search history.

(56) References Cited

U.S. PATENT DOCUMENTS 5,168,039 A * 12/1992 Crawford et al. ......... 536/24.32
5,631,130 A * 5/1997 Leckie et al. ................. 435/6
5,712,385 A    1/1998 McDonough et al. .... 536/24.32
5,731,150 A * 3/1998 Sandhu et al. ................ 435/6
6,251,638 B1    6/2001 Umansky et al. ........... 435/91.2
6,287,820 B1    9/2001 Umansky et al. ........... 435/91.1
6,368,800 B1 * 4/2002 Smith et al. .................... 435/6
6,492,144 B1    12/2002 Umansky et al. .......... 435/91.2
2002/0119478 A1    8/2002 Umansky et al. ............... 435/6

(Continued)

FOREIGN PATENT DOCUMENTS

WO    WO 95/04140    2/1995

(Continued)

OTHER PUBLICATIONS

Botezatu, I. et al. Clinical Chemistry 46(8):1078-1084 (2000).*

(Continued)

*Primary Examiner*—Diana B Johannsen
(74) *Attorney, Agent, or Firm*—Mintz Levin Cohn Ferris Glovsky and Popeo, P.C.; Ivor R. Elrifi; Matthew Pavao

(57) ABSTRACT

The present invention relates to a method for diagnosing and/or monitoring a bacterial or parasitic infection by detection and quantification of the transrenal nucleic acids, derived from bacterial pathogenic agents or from parasites, in urine. The detection method optionally includes the isolation and the purification of the nucleic acids from urine by methods known in the art including pairing with molecular probes that are specific for the pathogenic agents, PCR hybridization, PCR, nested PCR, SSCP, LCR, and SDA. Diagnostic kits based on these detection methods are also claimed.

10 Claims, 2 Drawing Sheets

U.S. PATENT DOCUMENTS

| | | | |
|---|---|---|---|
| 2003/0152591 A1 | 8/2003 | Sablon et al. | 424/225.1 |
| 2003/0152982 A1* | 8/2003 | De Beenhouwer et al. | 435/6 |
| 2004/0053264 A1 | 3/2004 | Park | 435/6 |
| 2006/0183108 A1* | 8/2006 | Melkonyan et al. | 435/5 |
| 2007/0037181 A1 | 2/2007 | Melkonyan et al. | 435/6 |

FOREIGN PATENT DOCUMENTS

| | | |
|---|---|---|
| WO | WO 98/54364 | 12/1998 |
| WO | WO 98/58086 | 12/1998 |
| WO | WO 2006/088895 | 8/2006 |
| WO | WO 2006/089203 | 8/2006 |

OTHER PUBLICATIONS

Su, Y.-H. et al. Ann. N.Y. Acad. Sci. 1022:81-89 (Jun. 2004).*
Sechi, L.A. et al. Molecular and Cellular Probes 11:281-285 (1997).*
Aceti et al. (1999), Thorax., 54:145-6.
Achtman et al. (1999), Molecular Microbiology 32:459-470.
Ahern (1995), The Scientist, 9:20-24.
Akopyanz et al. (1992), Nucleic Acids Res. 20:5137-5142.
Alm et al. (1999), Nature 397:176-180.
Al-Yatama et al. (2001), Prenatal Diagnosis, 21:399-402.
Atherton (1997), Gut 40:701-703.
Atherton et al. (1999), Current Microbiology 39:211-218.
Axon (1999), Gut 45(Supp. I): 1-14.
Barany (1991), Proc. Natl. Acad. Sci. USA, 88:189-193.
Bekkaoui et al. (1996), BioTechniques 20:240-248.
Belli et al. (1998), American Journal Tropical Medicine and Hygiene 58:102-109.
Bickley, et al. (1993), Journal of Medical Microbiology 39:338-344.
Blackwood et al.(2004), Journal of Clinical Microbiology 42:1626-1630.
Blaser et al. (1995), Cancer Research 55:2111-2115.
Botezatu et al. (2000), Clinical Chemistry 46:1078-1084.
Buffone et al. (1991), Clinical Chemistry 37:1945-1949.
Chan et al. (2003), Cancer Research 63:2028-2032.
Clayton et al. (1992), Journal of Clinical Microbiology 30:192-200.
Cover et al. (1994), The Journal of Biological Chemistry 269:10566-10573.
Del Portillo et al. (1991), Journal of Clinical Microbiology 29:2163-2168.
Disch et al. (2003), Transactions of the Royal Society of Tropical Medicine and Hygiene 97:391-395.
Disch et al. (2004), Acta Tropica 92:279-283.
Drago et al. (2002), Journal of Clinical Microbiology 40:4399.
Drobniewski et al., (2003), The Lancet Infectious Diseases 3:141-147.
Echavarria et al. (1998), Journal of Clinical Microbiology, 36:3323-3326.
Elzinga et al. (2004), The Lancet 363:814-819.
Fasanella et al. (2001), Vaccine 19:4214-4218.
Fenves (1985), Clinical Nephrology 23:96-100.
Frasier et al. (1992), Acta Virol., 36:83-89.
Friedlander (1978), Infection and Immunity, 22:148-154.
Gal et al. (2001), Annals New York Academy of Sciences 945:234-238.
Gorman et al. (1991), Molecular and Biochemical Parasitology 45:281-288.
Green et al. (1985), Infection and Immunity 49:291-297.
Haines et al. (1987), Postgraduate Medicine 81:77-79.
Hammer et al. (1992), Journal of Clinical Microbiology 30:54-58.
Hemal et al. (2000), Urology 56:570-574.
Higgins et al. (2003), Applied and Environmental Microbiology 69:593-599.
Ho et al. (1991), Journal of Clinical Microbiology 29:2543-2549.
Ho et al. (2005), Journal American Chemical Society 127:12673-12676.
Hurtle et al. (2004), Journal of Clinical Microbiology 42:179-185.
Jeong et al. (2004), Journal of Medical Virology, 72:281-289.
Kafwabulula et al. (2002), Int. J. Tuberc. Lung Dis. 6:732-737.
Keim et al. (2000), Journal of Bacteriology 182: 2928-2936.
Kleanthous et al. (1991), Molecular Microbiology 5:2377-2389.
Koide et al. (2005), Prenatal Diagnosis 25:604-607.
Kolk et al. (1992), Journal of Clinical Microbiology 30:2567-2575.
Kox et al. (1995), Neurology 45:2228-2232.
Lee et al. (2002), Cell Death and Differentiation 9:53-64.
Leppla (1995), Handbook of Natural Toxins. 8:543-572.
Li et al. (1990), The Lancet 335:1590-1591.
Lichtenstein et al. (2001), Annals New York Academy of Sciences, 945:239-249.
Lo (2000), Clinical Chemistry, 46:1039-1040.
Logan et al., (2004), Manual of Clinical Microbiology, 8th Ed, p. 445-460.
Lu et al. (1999), Journal of Clinical Microbiology 37:772-774.
Maiwald et al. (1995), European Journal of Clinical Microbiology and Infectious Diseases 14:25-33.
Maiwald et al. (1995), Infection 23:173-179.
Marei et al. (2003), Journal of Medical Microbiology 52:331-335.
Marmur et al. (1960), Biochemistry 46:453-461.
McCutchan et al. (1988), Molecular and Biochemical Parasitology 28:63-68.
Mercier et al. (1997), Molecular and Cellular Probes 11:89-94.
Mikesell et al. (2002), ASM News 49:320-322.
Mobley (1996), The American Journal of Medicine 100(Supp. 5A):5A-11S.
Moussa et al. (2000), The Journal of Urology 164:584-588.
Murdock et al. (1996), Clinical Infectious Diseases 23:475-480.
Navarre (2000), Cellular Microbiology 2:265-273.
Oggioni et al. (2002), Journal of Clinical Microbiology 40:3956-3963.
Piersimoni et al. (2002), Journal of Clinical Microbiology 40:4138-4142.
Piersimoni et al. (2003), Journal of Clinical Microbiology 41:5355-5365.
Pornthanakasem et al. (2001), BMC Cancer 1:2.
Poulter et al. (1981), Clinical Nephrology 15:216-220.
Qari et al. (1996), Molecular Phylogenetics and Evolution 6:157-165.
Qi et al. (2001), Applied and Environmental Microbiology 67:3720-3727.
Sarmiento et al. (2003), Journal of Clinical Microbiology 41:3233-3240.
Schürmann et al. (1983), Zbl. Bakt. Hyg., I. Abr. Orig. A 255:120-126.
Seah et al. (1995), Clinical and Diagnostic Virology, 4:113-120.
Shilo et al. (1981), Proc. Natl. Acad. Sci. USA 78:6789-6792.
Su et al. (2004), Journal of Molecular Diagnostics 6:101-107.
Su et al. (2004), Annals New York Academy of Sciences pp. 1022:81-89.
Tamarit et al. (2004), Journal of Clinical Virology 29:308-314.
Tomb et al. (1997), Nature 388:539-547.
Torrea et al. (2005), Journal of Medical Microbiology 54:39-44.
Tummuru et al. (1993), Infection and Immunity 61:1799-1809.
Uchida et al. (1986), Journal of General Microbiology 132:557-559.
Umansky et al. (1981), Biochimica et Biophysica Acta, 655:9-17.
Utting et al. (2002), Clinical Cancer Research 8:35-40.
Valentine et al. (1991), Journal of Clinical Microbiology 29:689-695.
van Vollenhoven et al. (1996), Urol. Res. 24:107-111.
Walker et al. (1994), Nucleic Acids Research 22:2670-2677.
Wang et al. (2004), Clinical Chemistry, 50: 211-213.
Waters et al. (1989), Nucleic Acids Research 17:2135.
Wegmüller et al. (1985), Arch Intern Med. 145:1711-1713.
Welkos (1991), Microbial Pathogenesis 10:183-198.
Zambardi et al. (1995), Molecular and Cellular Probes, 9:91-99.
International Search Report for PCT/US2006/005792, mailed Jan. 22, 2007.
International Search Report for PCT/US2006/005225, mailed Jan. 4, 2007.

* cited by examiner

SEQUENCE LISTING

```
<160> NUMBER OF SEQ ID NOS: 3

<210> SEQ ID NO 1
<211> LENGTH: 22
<212> TYPE: DNA
<213> ORGANISM: Artificial
<220> FEATURE:
<223> OTHER INFORMATION: Oligonucleotide primer

<400> SEQUENCE: 1
```

-continued

```
accagcacct aaccggctgt gg                                           22

<210> SEQ ID NO 2
<211> LENGTH: 22
<212> TYPE: DNA
<213> ORGANISM: Artificial
<220> FEATURE:
<223> OTHER INFORMATION: Oligonucleotide primer

<400> SEQUENCE: 2
catcgtggaa gcgacccgcc ag                                           22

<210> SEQ ID NO 3
<211> LENGTH: 22
<212> TYPE: DNA
<213> ORGANISM: Artificial
<220> FEATURE:
<223> OTHER INFORMATION: Oligonucleotide primer

<400> SEQUENCE: 3
gtaggcgaac cctgcccagg tc                                           22
```

KITS FOR DIAGNOSIS AND MONITORING OF PATHOGENIC INFECTION BY ANALYSIS OF CELL-FREE PATHOGENIC NUCLEIC ACIDS IN URINE

RELATED APPLICATIONS

This application claims priority to Italian patent application RM2005000068, filed Feb. 17, 2005, bearing attorney docket number 6627PTIT, which is incorporated herein by reference in its entirety.

FIELD OF THE INVENTION

Disclosed is a system for the diagnosis of infections caused by pathogenic agents, exemplified by tuberculosis and malaria, based on the molecular analysis of the transrenal nucleic acids (Tr-NA) detected in urine.

BACKGROUND OF THE INVENTION

Early analysis and the possibility of rapidly genotyping the pathogenic agent are among the principal objectives of research in the diagnostic field.

At present, the development of new diagnostic assays should take into consideration the following factors: compatibility to high-throughput screening methods; a higher degree of diagnostic sensitivity in the preliminary phase of the infection; and, particularly in developing countries, the ease of handling of biological samples, for more widespread distribution of their use.

There are currently three types of in vitro diagnostic systems: direct culture of the pathogenic agent from the biological sample, which is the so-called "gold standard" of diagnostic assays; immunological assays based on the detection of products or antigens of the infectious agent; and indirect immunological assays that can detect antibodies produced against the infectious agent during infection.

In the first system, the principal disadvantage is that the biological sample must be considered to be at risk for the transmission of the pathogenic agent, whereas in the latter case, there is no possibility of discriminating between past and current infections.

More recently, molecular diagnostic methods have been developed based on the detection of the nucleic acids of the pathogenic agent in the blood or plasma samples, or in the cell cultures, taken from the patient. These assays are generally much more sensitive than the immunological assays, and for this reason, and for their specificity, they are extremely promising. However, they may require the presence of special equipment and qualified personnel. Furthermore, the biological samples—in the case of plasma, blood, or cell cultures—are difficult to store unaltered, except under controlled temperature conditions.

Recently, molecular diagnostic methods based on transrenal DNA have been described for monitoring the progress of allogeneic transplants, to diagnose the sex of a fetus, and to detect the presence of tumoral markers. In particular, U.S. Pat. No. 6,251,638 describes an analytical method for detecting male fetal DNA in the urine of pregnant women; in U.S. Pat. No. 6,287,820, the system is aimed at the diagnosis of tumors, particularly of adenocarcinomas (of the colon and pancreas); and in U.S. Pat. No. 6,492,144, the Tr-DNA nucleic-acid analysis method is used to monitor the progress of allogeneic transplants, using known methods for the molecular analysis per se. The presence of identifiable transrenal DNA in urine, in fragments of nucleic-acid sequences (consisting of fewer than 1000 DNA base pairs) that cross the renal barrier, was also described in: Al-Yatama et al. (2001), "Detection of Y-chromosome-specific DNA in the plasma and urine of pregnant women using nested polymerase chain reaction" *Prenat Diagn,* 21:399-402; and in Utting, M., et al. (2002), "Microsatellite analysis of free tumor DNA in urine, serum, and plasma of patients: a minimally invasive method for the detection of bladder cancer"; *Clin Cancer Res,* 8:35-40.

Molecular detection of TrDNA in urine is performed in the same way as for other types of DNA, e.g., through PCR (polymerase chain reaction), nested PCR, hybridization, SSCP, LCR, SDA, or the so-called "cycling probe reaction".

The presence of transrenal DNA has been explained through the apoptosis phenomenon. During cell death most of the nuclear DNA is converted into nucleosomes and oligomers (Umansky, S. R., et al. [1982], "In vivo DNA degradation of thymocytes of gamma-irradiated or hydrocortisone-treated rats"; *Biochim. Biophys. Acta* 655:9-17), which are finally digested by macrophages or neighboring cells. However, a portion of this degraded DNA escapes phagocytic metabolism, and can be found in the bloodstream (Lichtenstein, A. V., et al. [2001], "Circulating nucleic acids and apoptosis"; *Ann NY Acad Sci,* 945:239-249), and, as confirmed in the above-indicated patents, also in urine.

The application of this system to bacteriological infections is not clear, because it has not been well studied and because prokaryotic DNA package is different from that of eukaryotic DNA. In the prior art, in contrast to the present method, the best-known system consists of isolating prokaryotic DNA from urine sediment that contains bacteria (Frasier, et al. [1992], "DNA probes for detecting *Coxiella burnetii* strains"; *Acta Virol,* 36:83-89). What happens to the prokaryotic DNA during infection is also well known. The prokaryotes are ingested by the cells of the immune system, such as macrophages and dendritic cells. The prokaryotes are then dissolved by the phagolysosome vesicles. The prokaryotic DNA is then released by the cell and a portion of this DNA enters the bloodstream in either of two ways: (a) the ingesting cell becomes apoptotic and breaks apart (Navarre, W. V. [2000], "Pathogen-induced apoptosis of macrophages: a common end for different pathogenic strategies"; *Cell Microbiol* 2:265-273); or (b) the phagolysosome vesicles release the fragments of the prokaryote (including the fragmented DNA) into the bloodstream (Friedlander, A. M. [1978], "DNA release as a direct measure of microbial killing by phagocytes"; *Infect Immune* 22:148-154).

The conclusion that can be drawn from these studies is that the diagnosis of the prokaryotic infection is made during the initial period of the infection. The same principle applies to parasitic infections, in which even less investigative work has been done on the effect of the infection in relation to the presence of DNA in urine. In the case of malaria, a diagnostic system that can function during the initial periods of the infection is not yet available. However, the need for such a system is recognized. In fact, at present, using current diagnostic systems, it is still difficult to distinguish between the presence of malaria in the initial period and viral hepatitis.

SUMMARY OF THE INVENTION

The diagnostic methods claimed herein are new methods for diagnosing or monitoring infectious diseases caused by bacterial or parasitic pathogenic agents by detecting and quantifying pathogen-related transrenal nucleic acid sequences.

These transrenal nucleic acids (Tr-NA) are smaller than 1000 base pairs (bp), e.g., smaller than 500 base pairs, smaller than 300 base pairs, smaller than 250 base pairs, or between 100 and 200 base pairs.

The method includes essentially the diagnosis and/or monitoring of an infection by detection and quantification of transrenal nucleic acid sequences in a urine sample. The nucleic acid sequences are specific to infectious agents, and are detected and quantitated (or quantified) by any methods known in the art, such as pairing with molecular probes that are specific for those pathogenic agents, hybridization, PCR, nested PCR, SSCP, LCR, and SDA.

The methods are applied to urine, with or without DNA isolation.

In embodiments of the invention, the methods can also include steps consisting of the fractionation of the sample, for example, through centrifuging or filtering, with the separation of a cell free fraction and of a fraction associated with the cell bodies. Furthermore, in another embodiment, the sample is pretreated with a denaturing agent.

The analysis of the nucleic acids is performed through one of the following techniques: hybridization of the nucleic acids, the cycling probe reaction, a polymerase chain reaction, a nested polymerase chain reaction, single-strand conformation polymorphism, a ligase chain reaction, strand displacement amplification, and restriction fragments length polymorphism.

In another of its embodiments, the invention relates to a kit for the diagnosis of DNA of the pathogenic agent in urine, including: reagents and/or materials for the separation and/or purification of transrenal DNA from a urine sample, DNA probes, or pairs of oligonucleotides (primers) that are specific for at least one pathogenic agent.

In its present form, the method is sufficiently sensitive to detect the initial phases of an infection. This fact has significant clinical implications, in view of the fact that most of the diagnostic errors involving tuberculosis or malaria have consequences that are felt in medical terms and also in economic and/or community terms among the populations that are at risk for contagion. For example, tuberculosis may already be infectious even if no clinical symptoms can be detected, and even if no confirmed findings have been provided by other diagnostic methods. The same thing has been found for malaria. Specifically, the transmission of sporozoites (the initial phase) is possible even when the symptoms can be diagnosed as those of viral hepatitis or have not yet been detected.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

Figure 1:
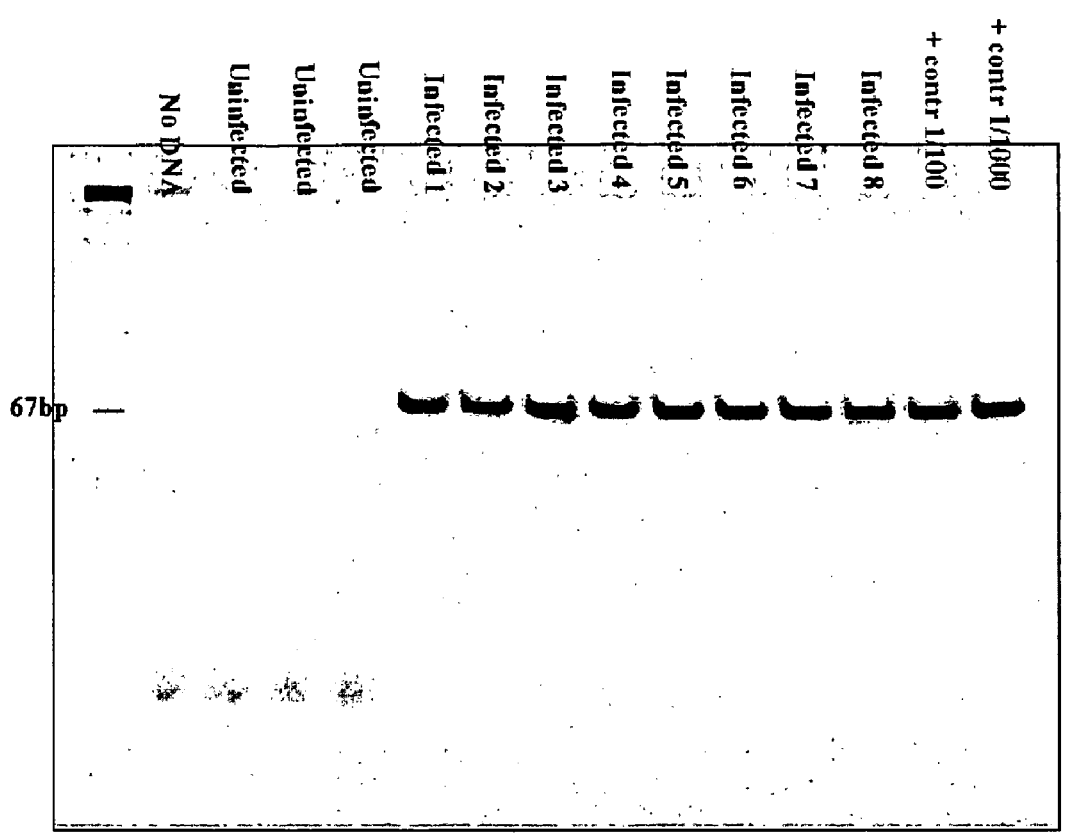
FIG. 1 is a photographic image showing the results of gel electrophoresis of DNA fragments amplified through two amplification cycles (semi-nested PCR) with the two pairs of primers SEQ ID NOs: 1 and 2 and SEQ ID NOs: 1 and 3, on samples of whole urine from patients diagnosed with pulmonary tuberculosis, using primers that are specific for *M tuberculosis*.

Other features and advantages of the invention will be apparent from the following detailed description and from the claims.

DETAILED DESCRIPTION OF THE INVENTION

The present definitions are offered for the purposes of the present invention:

Amplicon: Relatively small sequence of DNA, replicable via chain polymerization.

Amplification: Creation of additional copies of nucleic-acid sequences. Generally implemented using PCR or other methods known in the art (Dieffenbach & Dveksler, *PCR Primer: A Laboratory Manual*, Cold Spring Harbor Press, Plainview, N.Y. [1995]). This amplification method is often used in order to obtain a sufficient quantity of samples for other types of analysis.

Chaotropic: The property of substances (e.g., ions such as $SCN-$, $ClO4-$, and guanidine) that disturb the thermodynamic structure of water. It allows less polar and more hydrophobic substances to become more soluble in water. The effect at the biological level is the denaturation of proteins.

Complementarity/Complementary sequences: Sequences of polynucleotides that interact with each other, depending on the interaction between the bases. For example, the AGT sequence is complementary to TCA. It is possible to have a fully or partially complementary sequence, and this is what determines the efficiency or attractive force between the two sequences. Average complementarity would prevent a strong complementarity from hybridizing, under conditions that would allow it to remain attached.

Deletion: Variation in a nucleotide or amino-acid sequence, in which one or more of the nucleotides or amino acids in the original sequence are missing.

Gene: DNA sequence that contains sequences necessary to code for an mRNA through transcription, and to control the expression of these sequences.

Genome: The total set of genes of an organism enclosed, among the eukaryotes, in chromosomal structures.

Homolog: Term that defines the level of complementarity or similarity between two sequences.

Hybridization: Method that allows two nucleic-acid sequences to recognize each other as complementary and to join together (annealing). This ability of nucleic sequences is a well-known phenomenon. The first hybridization method was described in Marmur & Lane, *PNAS USA*, 46:453 (1960) and 461 (1960), but since then has been perfected as a technique in molecular biology. Today, the term "hybridization" includes, among others, slot/dot and blot hybridization. The conditions that allow nucleotide sequences to recognize each other (hybridization) can be modified in such a way as to produce complete hybridization (complementarity with high specificity) or partial hybridization (complementarity with average specificity). In the present application, whenever the term "hybridization" is used, the conditions should be understood as referring to those that allow average or high complementarity. The technician in the field can calculate how many artificial sequences are needed to encourage hybridization between two complementary sequences in the opposite direction, known as antiparallel association.

Insertion/Addition: Change in a nucleotide or amino-acid sequence that results in the addition of one or more nucleotides or amino acids to the original sequence.

Label/Tag: Any molecule or atom that can emit a signal and that can be attached to a protein or nucleic acid. This emitted signal may be of any type.

Ligase Chain Reaction: A method of DNA amplification similar to PCR. LCR differs from PCR because it amplifies the probe molecule rather than producing amplicon through polymerization of nucleotides. Two probes are used per each DNA strand and are ligated together to form a single probe. LCR uses both a DNA polymerase enzyme and a DNA ligase enzyme to drive the reaction. Like PCR, LCR requires a thermal cycler to drive the reaction and each cycle results in a doubling of the target nucleic acid molecule. LCR can have greater specificity than PCR.

Nested PCR: A second PCR which is performed on the product of an earlier PCR using primer, which are internal to the originals. This significantly improves the sensitivity and specificity of the PCR.

Nested primer: A selected primer internal to an amplicon obtained with a first PCR cycle. The amplification process that uses at least one nested primer improves specificity, because the non-specific products of the first cycle are not amplified in the second cycle, because they lack the sequence that corresponds to the nested primer.

Nucleic acid: Refers to an oligonucleotide, nucleotide, polynucleotide, or fragments/parts thereof and to DNA or RNA of natural (e.g., genomic) or synthetic origin. It may have a double or single helix, and may also represent the sense or antisense direction of a sequence. Parallel helix (5→3'); anti-parallel helix (3→5').

Oligonucleotide/Polynucleotide/Nucleic-acid polymer: These terms are equivalent, and are understood as referring to a molecule consisting of more than two deoxyribonucleic or ribonucleic acid bases. The number of nucleotides (bases) and the length of the oligonucleotide fragment may vary. They may be synthesized in different ways. The sequences are traditionally defined as starting with 5' and ending with a 3'. These numbers indicate the direction of the sequence.

Pathogenic agent: The term "pathogenic agent" refers to bacteria and parasites, including bacterial agents and eukaryotic organisms capable of causing an infection, respectively.

Pellet: Sediment that, when cells are present, usually includes the cell fraction, or that can be obtained by centrifuging a sample at a speed between 3000 g and 4000 g.

Polymerase: Enzyme utilized in the amplification of specific nucleic acids. The term includes all of the polymerase variants, from DNA polymerases to Taq (*Thermus aquaticus*) polymerases.

Primer: Oligonucleotide from which, under proper conditions, the synthesis of a polynucleotide sequence can be initiated. A primer may exist naturally (for example, in an enzymatic digestion of a polynucleotide), or may be obtained through chemical synthesis.

Probe: Oligonucleotide that can be produced artificially or naturally, and that forms a combination with another nucleic-acid sequence. The probes are useful in discovering specific sequences in a sample containing unknown DNA. In this patent, all of the probes can be bound to a signaling molecule (or reporter). The reporter molecule makes it possible to detect the probe (for example, through enzymatic reactions (e.g., ELISA [Enzyme-Linked Immunosorbent Assay]), radioactivity, fluorescence, or other systems).

Purification/Decontamination/Sterilization: Refers to a process for removing contaminants from a sample, where the result is a sample containing 50%, 60%, 75%, 90% or over 90% of the material toward which the purification procedure is directed.

Restriction enzyme/Restriction endonucleases: Prokaryotic enzymes that cut double-helix nucleic-acid sequences, or that produce cuts near specific nucleotide sequences.

Sample: The term is broadly interpreted and includes any form that contains nucleic acids (DNA or RNA) in solution or attached to a solid substrate, where the definition of "nucleic acids" includes genomic DNA (for example, when it is attached to a solid substrate, such as in the Southern Blot or in solution), cDNA, and other forms.

Combinations of two nucleic-acid sequences through hybridization are formed thanks to the hydrogen bonds between G and C or A and T bases or analogs of these bases. These combinations are complementary, and the DNA helixes are anti-parallel. This hybridization combination can be created with one sequence (or helix) in a solution and the other attached to a solid phase (such as, for example, in the FISH [fluorescent in situ hybridization] method), or else with both of the sequences in solution.

Severity/Stringency: For stringent temperature conditions in the case of nucleic-acid hybridization, these terms usually refer to a variable temperature between a maximum, for a nucleic acid, represented by Tm less 5° C., and a minimum represented by Tm less 25° C. The technique used in the field utilizes stringent temperature conditions, in combination with other parameters (e.g., saline concentration), to distinguish sequences with a quasi-exact homology.

Substitution: Change in a sequence of one or more nucleotides or amino acids with another nucleotide or amino acid, respectively.

Target sequence: Nucleic-acid sequence that should be analyzed through hybridization, amplification, or other methods or combinations of methods.

Tm (melting temperature): Temperature at which a specific double-helix DNA population dissociates into single-helix sequences. The formula for calculating this temperature for polynucleotide fragments is well known in the art: Tm=81.5+0.41 (% G+C) (Anderson & Young, "Quantitative Filter Hybridization," in *Nucleic Acid Hybridization* [1985]). For oligonucleotides with fewer than 40 base pairs, a simplified formula can be used: Tm=3° C.×(G+C)+2×(A+T).

Tr-DNA/RNA: Transrenal DNA/RNA, or DNA/RNA present in urine after having been passed through the kidney barrier.

Urinary tract: Includes the organs and ducts that participate in the elimination of urine from the body.

Transrenal Nucleic Acids (TrNAs) in Pathogenic Infection

The present invention describes a method for diagnosing and/or monitoring of a bacterial or parasitic infection by detecting and quantification of the transrenal nucleic acids of pathogenic agents in urine. It has been discovered that the nucleic acids of these pathogenic agents cross the transrenal barrier (Tr-NA) and can be detected in urine as low-molecular-weight fragments (consisting of fragments whose length is less than 1000 nucleotides) through molecular methods known in the art.

The presence of transrenal nucleic acids (Tr-NA) in urine was detected previously only in hosts who had undergone heterologous tissue or organ transplants, in the case of women pregnant with male fetuses, and in the case of tumors characterized by specific marker genes.

The presence of transrenal nucleic acids in the case of infections caused by pathogenic agents according to the present invention also relates to infections that do not directly involve the urinary tract, even in the absence of hematuria or of pathologies that lead to the rupture, or that alter the normal integrity, of the renal barrier. Generally, the transrenal nucleic acids (Tr-NA) according to the invention are not associated with, and are not derived from, the DNA of cells that are lost or released in the urinary tract. Instead, the nucleic acids that are detected in the present invention are generally filtered by the glomerular-renal filtration mechanism. Thus, their lengths are smaller than about 1000 base pairs, e.g., smaller than about 500, smaller than about 300, smaller than about 250, or between about 100 and about 200 bases or base pairs, as opposed to other cases in which DNA usually has a longer length, greater than 1000 bases or base pairs. In embodiments, the Tr-NAs are DNA fragments.

Therefore, in the present invention, the transrenal nucleic acid (TrNA) is not found in the urine sediment, but in the soluble fraction, although a small amount of TrNA can co-sediment with the cells during centrifuging, which is performed at a speed between 3000 g and 5000 g, e.g., between 3500 g and 4500 g.

Thus, the discovery makes it possible, for the first time, to confirm the presence of Tr-NA derived from pathogenic agents directly in urine, and thus is applicable to the diagnosis of all infectious diseases with a bacterial or parasitic etiology.

Thus, in an embodiment, the invention relates to a method for the diagnosis a bacterial or parasitic infection in a subject by detection of pathogen-related transrenal nucleic acids in a urine sample from the subject. In embodiments, the invention further includes the step of quantifying the pathogen-related transrenal nucleic acids. In other embodiments, the invention provides for methods of monitoring a bacterial or parasitic infection by repeated detection of pathogen-related transrenal nucleic acids in a subject over a period of time.

In an embodiment, the invention relates to a method for diagnosis of an infection in a subject, including the step of detection of the presence pathogen-related transrenal nucleic-acid sequences in a urine sample of the subject. In a further embodiment, the invention relates to the above method in which the transrenal nucleic acids are isolated from the urine sample prior to detecting the nucleic acids.

In another embodiment, the invention relates to the above method of diagnosing and/or monitoring a bacterial or parasitic infection in which the bacterial or parasitic infectious agent is *Mycobacterium tuberculosis* DNA In yet another embodiment, the method according to the invention may include an initial treatment of the urine sample prior to detection. In a specific embodiment, the invention includes the pretreatment of the urine sample with agents that inhibit the degradation of the nucleotide sequences. Included are the enzymatic inhibitors, such as chelating agents, detergents, or denaturing agents, and preferably DNase or RNase inhibitors, which include EDTA, guanidine HCl, guanidine isothiocyanate, N-lauryl sarcosine, and sodium dodecyl sulfate.

According to another embodiment, the urine sample may be centrifuged (at a speed between 3000 g and 5000 g, such as between 3500 g and 4500 g) or ultrafiltered in order to separate the fraction consisting of cells and their fragments from the supernatant containing the soluble DNA or RNA. However, the urine sample may also be utilized without this fractionation.

The optional isolation or purification and quantification of the transrenal nucleic acids are achieved through the use of chemical or physical methods that are already known in the art. It includes at least one purification step, using methods selected from among extraction with organic solvents, filtration, precipitation, absorption on solid matrices, affinity chromatography (e.g., via ion exchange), or else molecular exclusion chromatography or combinations of these methods.

However, the purification method must be appropriate for the isolation of DNA (single- or double-helix) that are less than 1000 nucleotides in length, with a corresponding molecular weight, assuming, as the average molecular weight, that of a nucleotide having a value of 330 Daltons. In some embodiments, the purification is specific for fragments that are smaller than 500 nucleotides (nt) in length, with a corresponding molecular weight, such as fragments whose lengths are less than 300 nt, fragments less than 250 nt in length, or fragments whose lengths are between 100 and 200 base pairs of nucleic acids (nt).

In an embodiment, the DNA isolation method is implemented by pretreating the urine sample with a denaturing agent, such as urea, guanidine HCl, or guanidine isothiocyanate, at room temperature. Guanidine isothiocyanate is utilized. The sample is then caused to pass through a solid phase, such as a matrix consisting of a silica-based resin which, in the presence of chaotropic salts, such as guanidine isothiocyanate, binds the nucleic acids. Even more preferably, a resin such as Wizard Purification Resin® (Promega®) is utilized. The sample is then collected or eluted in a buffer, such as Tris-EDTA (Tris 10 mM, EDTA 1 mM), or in water.

In a preferred embodiment, the characterization and the determination of the presence of DNA of the pathogenic agent in step b) is performed through a technique selected from the group consisting of: hybridization of the nucleic acids, a cycling probe reaction (F. Bekkaoui et al., in *BioTechniques* 20:240-248 [1996]), a polymerase chain reaction (*PCR Protocols: A Guide to Methods and Applications*, by M. Innis et al.; Elsevier Publications, 1990), a nested polymerase chain reaction, single-strand conformation polymorphism, or ligase chain reaction (LCR) (F. Barany, in *PNAS USA*, 88:189-93 [1991]), strand displacement amplification (SDA) (G. K. Terrance Walker, et al., in *Nucleic Acid Res*, 22:2670-77 [1994], and restriction fragments length polymorphism. Polymerase chain reaction (PCR) is the preferred method for the detection or analysis of nucleic acids. More preferred is dual-amplification PCR, with the use of a nested primer in nested or semi-nested PCR (reference: bio.davidson.edu/courses/genomics/method/NestedPCR.html).

One of the preferred embodiments of the invention is a diagnostic method that utilizes the detection method. In particular, the method preferably applies to the following prokaryote genera: *Brucella, Treponema, Mycobacterium, Listeria, Legionella, Helicobacter, Streptococcus, Neisseria, Clostridium, Staphylococcus* and *Bacillus*; and more preferably to *Treponema pallidum, Mycobacterium tuberculosis*,

*Mycobacterium leprae, Listeria monocytogenes, Legionella pneumophila, Helicobacter pylori, Streptococcus pneumoniae, Neisseria meningitis, Clostridium novyi, Clostridium botulinum, Staphylococcus aureus*, and *Bacillus anthracis*.

The method applies particularly to the following protozoan or metazoan genera: Trichomonas, *Toxoplasma, Giardia, Cryptosporidium, Plasmodium, Leishmania, Trypanosoma, Entamoeba, Schistosoma, Filariae, Ascaria*, and *Fasciola*; and more preferably to *Trichomonas vaginalis, Toxoplasma gondii, Giardia intestinalis, Cryptosporidium parva, Plasmodium, Leishmania, Trypanosoma cruzi, Entamoeba histolytica, Schistosoma, Filariae, Ascaria*, and *Fasciola hepatica*.

Particularly preferred infectious agents are bacteria in the genus *Mycobacterium*.

The method is preferably applied to *Mycobacterium tuberculosis*, with the selection, for detection purposes, of probes or oligonucleotide primers containing oligonucleotides in the sequence IS 6110 (a gene present in the genome of *Mycobacterium tuberculosis*). A particularly preferred pair of primers is the one consisting of sequence IDN 1 and IDN 2 for the first amplification cycle, and sequence IDN 1 and IDN 3 for the second amplification cycle, when the detection is performed via a semi-nested polymerase chain reaction (semi-nested PCR). The same method can also be applied at the genus level, e.g., by using an oligonucleotide primer based on an rRNA sequence that is common to all genuses of *Mycobacterium*, but species-specific primers (e.g., IDN 1, 2, and 3) may also be selected.

In another of its embodiments, the invention relates to a kit for the diagnosis of DNA of a pathogenic agent, or of a bacterium or parasite, in urine, which kit includes reagents and/or materials for the separation and/or purification of transrenal DNA from a urine sample, DNA probes, or pairs of oligonucleotides (primers) that are specific for at least one pathogenic agent. Reaction tubes, denaturing agents for the pretreatment of the sample, enzymes for marking the probe, and enzymes for the amplification of the DNA may optionally be present. In a preferred embodiment, the kit includes oligonucleotide pairs (primers) and reagents that are specific for the polymerization chain reaction.

EXAMPLES

All of the methodology described herein may be modified by the technician in the field with no change in the basic principal idea.

Example 1

Stabilization and Preparation of the Samples

The first step in this method is the preparation of the DNA present in the urine sample. This method was described previously in studies of the detection of transrenal DNA in urine. All of the preparation takes place at room temperature (on the order of 24° C.).

A quantity consisting of approximately 50 to 60 ml of urine is collected from the patient in sterile containers.

Within 30 minutes after collection of the urine, 0.5M EDTA and 0.5M Tris-HCl (at a pH of 8.5) are added until a final concentration of 10 mM is reached. The purpose is to inhibit possible nuclease enzymes. Specifically, the EDTA is added to inhibit nucleases that are dependent on divalent ions, and the Tris-HCl is added so that a pH value can be reached that inhibits acid nucleases. This stabilizes the specimen, in the sense that it stabilizes the DNA fragments.

The samples are then divided into aliquot portions of 5 ml and stored at a temperature of −80° C.

In certain cases, prior to separation or stabilization, the urine samples were centrifuged for 15 minutes at 4000 g, and the supernatant or the pellet was then treated separately in order to extract and analyze the DNA that was present.

Example 2

Isolation and Purification of the Nucleic Acids

Because the idea is to analyze DNA fragments whose length is less than 1000 nucleotides, and preferably less than 500, and more preferably less than 300, and yet more preferably less than 200, and even yet more preferably between 100 and 200 nucleotides, the commercially available DNA isolation kits cannot be used, because they are based on the isolation of DNA having a higher molecular weight.

All of the steps in the following method take place at room temperature (20 to 25° C.). As mentioned above, the sample may consist of aliquot parts of urine, or else of the urine supernatant or of the sediment.

2 volumes of GITC [guanidine isothiocyanate] (at a concentration of 6M) were added to 1 volume consisting of 5 ml of sample and mixed well.

The DNA whose length is less than 1000 base pairs of nucleic acids, and preferably less than 500, and more preferably less than 300, and yet more preferably less than 200, and even yet more preferably between 100 and 200 base pairs, was then separated via immobilization on a Wizard Resin Suspension® (Promega®) matrix, which consists of a silica-based resin which, in the presence of chaotropic salts (the guanidine isothiocyanate) binds the nucleic acids. The DNA was then eluted from the resin with water, or else with 10 mM Tris-HCl at a pH of 7.5 and 1 mM EDTA.

The method described hereinabove yields reproducible results.

Example 3

Preparation for PCR

The PCR primers are usually constructed for amplicons measuring 60 to 120 nt or 250 to 400 nt. In this case, it was necessary to find primers that could also function for sequences consisting of 150 to 250 nt.

The FastPCR method (biocenter.helsinki.fi/bi/bare-1_html/oligos.htm) was used to design the primer sequences based on the complete human genome sequence.

The Primer 3 method (frodo.wi.mit.edu/cgi-bin/primer3/primer3_www.cgi) was utilized to select the nested (semi-nested) primer.

This method was used to create tuberculosis primers. The primer that was constructed for tuberculosis was reciprocal to the sequence IS 6110, which is present only in the *Mycobacterium tuberculosis* genome, as indicated below:

```
IDN 1 F-785:  ACCAGCACCTAACCGGCTGTGG    (SEQ ID NO: 1)
and

IDN 2 R-913:  CATCGTGGAAGCGACCCGCCAG.   (SEQ ID NO: 2)
(Product: 129 nt)
```

Instead, for the nested primer, the following sequence was selected:

```
IDN 1 F-785:  ACCAGCACCTAACCGGCTGTGG    (SEQ ID NO: 1)
and

IDN 3 R-851:  GTAGGCGAACCCTGCCCAGGTC.   (SEQ ID NO: 3)
(Product: 67 nt)
```

Example 4

Diagnosis of Tuberculosis

The methodology described above was applied with the utilization of patients infected with pulmonary tuberculosis. It is important to note that the *Mycobacterium* can also infect other organs, such as the liver, the kidneys, the spinal fluid, and others. Consequently, the patients were selected specifically for infection with pulmonary tuberculosis, but with no renal infections.

Eight samples were prepared using the methodology described above, from 8 patients who were selected because of their specifically pulmonary tuberculosis.

FIG. 1 illustrates the electrophoresis of the DNA fragments that were amplified via two amplification cycles (semi-nested PCR). The fragments were amplified with the 1&2 primer pair and then with the 1&3 primer pair, for 20 and 35 cycles, respectively. As can be seen, the primers amplified the tuberculosis DNA in 8 of the 8 patients who participated in the experiment. None of the control (non-infected) patients was found to be positive for tuberculosis.

Example 5

Diagnosis of Tuberculosis in Centrifuged Fractions

As in Example 4, the methodology described above was applied with the utilization of patients infected with pulmonary tuberculosis. Eight samples were prepared using the methodology described above, from 8 patients who were selected because of their specifically pulmonary tuberculosis.

These 8 samples were fractionated, via centrifugation, into 8 samples consisting of the supernatants and 8 samples consisting of pellets.

Figure 2:
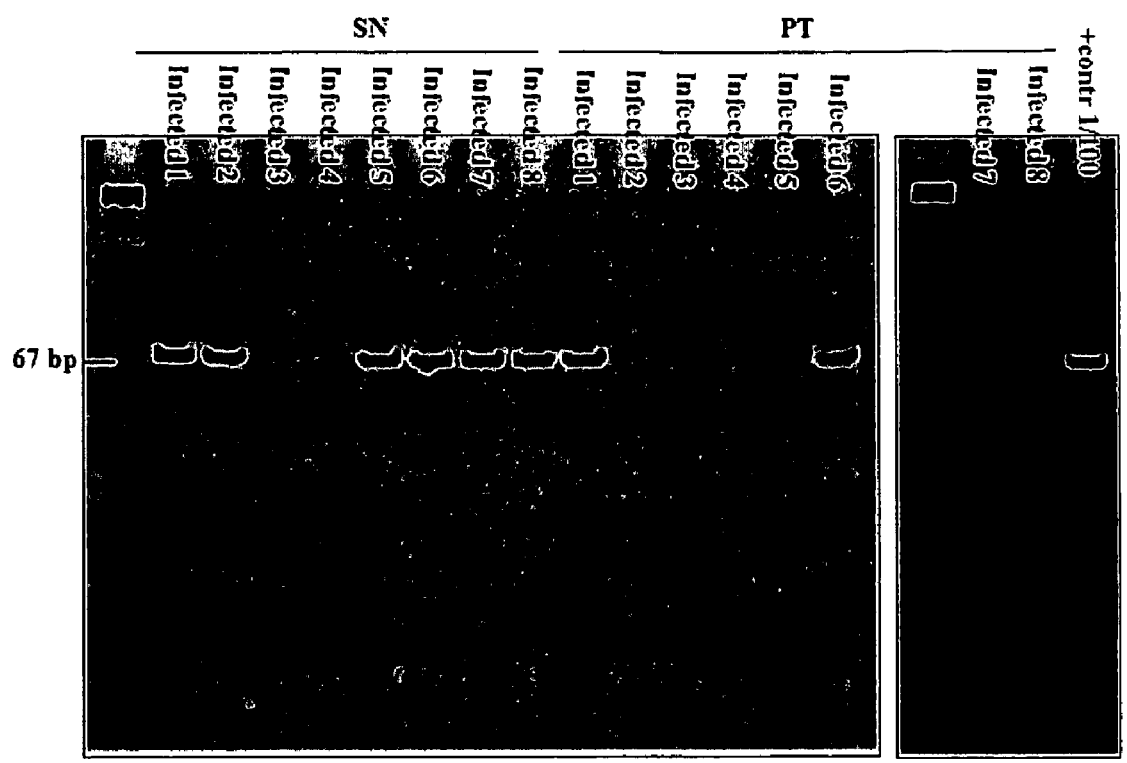
FIG. 2 is a photographic image showing the results of gel electrophoresis of DNA fragments amplified through two amplification cycles (semi-nested PCR) on samples of fractionated urine (supernatant and pellet) from patients with pulmonary tuberculosis, using primers that are specific for *Mycobacterium tuberculosis*, pairs of primers with SEQ ID NOs: 1 and 2 and SEQ ID NOs: 1 and 3.

FIG. 2 illustrates the electrophoresis of the DNA fragments that were amplified via two amplification cycles (semi-nested PCR) from urine samples, provided by patients with tuberculosis, that were fractionated into supernatants and pellets. The primers that were utilized consisted of primers that were specific for the *M tuberculosis* sequence IS 6110, i.e., the primers of SEQ ID NOs: 1 and 2 and the SEQ ID NOs: 1 and 3, which are nested primer pairs (semi-nested PCR). The primers for the first and second cycles were selected for their specificity for *Mycobacterium tuberculosis*, with the recognition of part of the bacterium's sequence IS 6110. This primer was utilized for 20 cycles, and then the nested primer was utilized for 35 cycles, to produce the DNA sample consisting of 67 nt that is shown in the figure.

The results show that 6 of 8 of the supernatant samples display the presence of *M tuberculosis* DNA, whereas only 2 of 8 of the pellet samples display the presence of the DNA of this bacterium. It can be inferred from these results that, although the fractionation method is not yet as refined as the method that uses the whole sample, the Tr-DNA is found in the supernatant sample in a majority of instances. Nevertheless, it can be seen that the primer utilized in this semi-nested PCR reaction has a demonstrated specificity of 6/8 (75%) for a specific species (namely, *M tuberculosis*).

Sequences Identified

```
IDN 1 F-785:  ACCAGCACCTAACCGGCTGTGG    (SEQ ID NO: 1)

IDN 2 R-913:  CATCGTGGAAGCGACCCGCCAG    (SEQ ID NO: 2)

IDN 3 R-851:  GTAGGCGAACCCTGCCCAGGTC.   (SEQ ID NO: 3)
```

EQUIVALENTS

Although particular embodiments have been disclosed herein in detail, this has been done by way of example for purposes of illustration only, and is not intended to be limiting with respect to the precise form of the disclosed invention or to the scope of the appended claims that follow. In particular, it is contemplated by the inventors that various substitutions, alterations, and modifications may be made to the invention without departing from the spirit and scope of the invention as defined by the claims. Various alterations and modifications of the invention are believed to be a matter of routine for a person of ordinary skill in the art with knowledge of the embodiments described herein. Other aspects, advantages, and modifications considered to be within the scope of the following claims.

---

The invention claimed is:

1. A kit, comprising:
   a) one or more reagents or materials for the isolation and purification of cell-free pathogen-related transrenal nucleic acids from a urine sample of a subject, wherein said reagents or materials comprise a matrix including a silica-based resin, wherein said silica-based resin isolates cell-free nucleic acids that are less than about 300 nucleotides; and wherein said reagents or materials comprise an agent that inhibits the degradation of the cell-free nucleic acids; and
   b) two or more primers for detecting said cell-free pathogen-related nucleic acids in said urine sample, wherein said two or more primers are selected from the group consisting of SEQ ID NOs: 1-3.

2. The kit according to claim 1, further comprising reagents for the performance of a technique selected from the group consisting of a hybridization of said cell-free pathogen-related nucleic acids, a cycling probe reaction, a polymerase chain reaction, a nested polymerase chain reaction, a ligase chain reaction, and a strand displacement amplification.

3. The kit according to claim 1, further comprising a chaotropic agent.

4. The kit according to claim 1, wherein said agent that inhibits the degradation of the nucleic acids is selected from the group consisting of a ion-chelating agent, a denaturing agent, and an ionic detergent.

5. The kit according to claim 4, wherein said ion-chelating agent is EDTA; said denaturing agent is guanidine HCL or guanidine isothiocyanate; and said ionic detergent is N-lauryl sarcosine or sodium dodecyl sulfate.

6. A kit, comprising:
   a) one or more reagents or materials for the detection and quantitation of cell-free pathogen-related nucleic acids from a urine sample of a subject, wherein said reagents or materials comprise a matrix including a silica-based resin, wherein said silica-based resin isolates cell-free nucleic acids that are less than about 300 nucleotides; and wherein said reagents or materials comprise an agent that inhibits the degradation of the cell-free nucleic acids; and
   b) two or more primers for detecting and quantitating said cell-free pathogen-related nucleic acids in said urine sample, wherein said two or more primers are selected from the group consisting of SEQ ID NOs: 1-3.

7. The kit according to claim 6 further comprising reagents for the performance of a technique selected from the group consisting of a hybridization of said cell-free pathogen related nucleic acids, a cycling probe reaction, a polymerase chain reaction, a nested polymerase chain reaction, a ligase chain reaction, and a strand displacement amplification.

8. The kit according to claim 7, further comprising a chaotropic agent.

9. The kit according to claim 6, wherein said agent that inhibits the degradation of nucleic acids is selected from the group consisting of a ion-chelating agent, a denaturing agent, and an ionic detergent.

10. The kit according to claim 9, wherein said ion-chelating agent is EDTA; said denaturing agent is guanidine HCL or guanidine isothiocyanate; and said ionic detergent is N-lauryl sarcosine or sodium dodecyl sulfate.

* * * * *